US006432534B1

(12) United States Patent
Hayakawa et al.

(10) Patent No.: US 6,432,534 B1
(45) Date of Patent: Aug. 13, 2002

(54) PROCESS FOR THE PRODUCTION OF TABLETS AND TABLETS

(75) Inventors: Eiji Hayakawa, Susono; Motohiro Ohta, Sunto-gun; Hiroyuki Morimoto, Tokyo; Kiyoshi Morimoto, Mishima; Yasushi Watanabe, Numazu; Kunio Ito, Sunto-gun; Sanji Tokuno, Tokyo, all of (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/555,660

(22) PCT Filed: Dec. 3, 1998

(86) PCT No.: PCT/JP98/05474

§ 371 (c)(1),
(2), (4) Date: Sep. 14, 2000

(87) PCT Pub. No.: WO99/27887

PCT Pub. Date: Jun. 10, 1999

(30) Foreign Application Priority Data

Dec. 3, 1997 (JP) ........................................ 9-332812

(51) Int. Cl.[7] ........................... B32B 5/16; B27N 3/08; A61K 9/20

(52) U.S. Cl. ....................... 428/403; 264/109; 264/299; 264/309; 264/319; 424/465; 424/474

(58) Field of Search ............................... 264/109, 299, 264/309, 319; 428/402, 403; 424/464, 465, 474

(56) References Cited

U.S. PATENT DOCUMENTS

| | | | | | |
|---|---|---|---|---|---|
| 4,323,530 | A | * | 4/1982 | Voss et al. | 264/109 |
| 5,017,122 | A | * | 5/1991 | Staniforth | 425/100 |
| 5,056,623 | A | * | 10/1991 | Glasel et al. | 184/7.4 |
| 5,407,339 | A | * | 4/1995 | Fehlhafer | 425/106 |
| 5,643,630 | A | * | 7/1997 | Hinzpeter et al. | 427/133 |
| 6,036,974 | A | * | 3/2000 | Tsushima et al. | 424/464 |

* cited by examiner

*Primary Examiner*—Hoa T. Le
(74) *Attorney, Agent, or Firm*—Fitzpatrick, Cella, Harper & Scinto

(57) ABSTRACT

A method for producing tablet including active component, diluting agent, and lubricant by means of a tabletting machine provided with punches and dies, comprising steps of; preparing molding material including active component, diluting anent, and a part of lubricant; applying most of the remaining amount of the lubricant on surfaces of the punches and a surface of the die; and tabletting the molding material by means of the punches on which surfaces the lubricant is applied and the die on which surface the lubricant is applied

14 Claims, 9 Drawing Sheets

(a)

(b)

(a)

(b)

(a)

(b)

(a)

(b)

(c)

(a)

(b)

(c)

PROCESS FOR THE PRODUCTION OF TABLETS AND TABLETS

TECHNICAL FIELD

The present invention relates to a tablet production method and a tablet, specifically to a tablet production method wherein molding material is hardly adhered on a punch and a die of a tabletting machine so that material can be continuously tabletted for a long time and disintegration time and hardness of produced tablet is the same as that of a tablet produced by an internal lubricant method and to a newly constructed tablet which can be produced by such a method.

BACKGROUND ART

A tablet is a very useful pharmaceuticals for carrying and dosing and is easy to be taken for an elder person or a patient because it doesn't float on the water when dosing with water. Further, it has many advantages such that production cost of a tablet can be held down. Therefore, it is a most multipurpose dosage form for internal application and oral application.

Such a tablet is generally produced by a compression method.

However, when a tablet is produced by a compression method, there have been problems such that molding material is adhered on the punch and the dies of the tabletting machine to cause gride between the punch and the dies and sticking, capping, and laminating are apt to be caused.

In order to solve such problems, lubricant such as magnesium stearate, lauryl sodium sulphate, talc and so on are mixed in the molding material to be tabletted other than active component and diluting agent and the mixture is compressed to obtain a tablet so as to prevent that molding material to be tabletted is apt to attach on the punches and dies and gride between the punch and die is apt to be caused, to execute smooth tabletting, and to prevent defective goods (hereinafter, this tablet production method is called as "an internal lubricant method").

On the other hand, it is advisable that adequate amount of lubricant is attached on the surfaces of the punches, the dies, and a tablet in order to prevent adhering of the molding material to be tabletted on the punches and the dies of the tabletting machine. Lubricant isn't required to be contained in the tablet.

Based on these idea, there is a so called external tablet spraying method disclosed in for example JP-B-41-11273, JP-A-56-14098, and JP-A-7-124231 as a technique wherein the molding material to be tabletted is prevented from adhering on the punches and the dies of the tabletting machine while tabletting and the produced tablet is prevented from causing sticking and so on.

FIG. 7 schematically shows the procedures of the prior tablet production method disclosed in JP-B-41-11273.

According to this method, lubricant L is sprayed by air pressure from a spray nozzle 55 to a surface (lower surface) 53*s* of an upper punch 53 and a surface (upper surface) 54*s* of a lower punch 54 as shown in FIG. 7(*a*). Then, molding material m is charged in a die 51 provided for a rotary table 52 in the procedure shown in FIG. 7(*b*). Further, the molding material m is compressed to produce a tablet by means of the upper punch 53 of which surface (lower surface) 53*s* is applied with lubricant and the lower punch 4 of which surface (upper surface) 54*s* is applied with lubricant as shown in FIG. 7(*c*).

FIG. 8 schematically shows the procedures of the prior tablet production method disclosed in JP-A-56-14098.

According to this method, lubricant L is sprayed in a spray 56 provided above a die 51 of a rotary table 52 as shown in FIG. 8(*a*).

Then, lubricant L is placed on a surface (upper surface) 54*s* of a lower punch 54 as shown in FIG. 8(*b*). Compressed air is sprayed against the lower punch 54 from a nozzle 58 provided in a spraying chamber 57 which is provided separately from the spray 56. The lubricant L on the lower punch 54 is blown to be dispersed and the dispersed lubricant L is attached on a surface (inner wall) 51*s* of the die 51 and the surface (lower surface) 53*s* of the upper punch 53 as shown in FIG. 8(*c*). Accordingly, molding material (not shown) is compressed to produce a tablet by means of the die 51, the upper punch 53, and the lower punch 54 of which surface (inner wall) 51*s*, the surface (lower surface) 53*s*, and the surface (upper surface) 54*s* are lubricated.

However, according to the production methods described in JP-B-41-11273 and JP-A-56-14098, it has been impossible to apply lubricant L uniformly and stably on the surface (inner wall) 51*s* of the die 51, the surface (lower surface) 53*s* of the upper punch 53, and the surface (upper surface) 54*s* of the lower punch for a long time of tabletting. Therefore, they has problem such that they can't be executed as an industrial production method.

The tablet production method disclosed in Jp-A-7-124231 has been proposed by the present inventors in order to solve the above-mentioned problems.

FIG. 9 schematically shows the procedures of the tablet production method disclosed in JP-A-7-124231.

According to this method, a tabletting machine in which a pulsating vibration air generation means 67 is connected above the die 51 before a step for charging molding material in the die 51 and a spraying chamber 58 having a spray nozzle 59 for spraying lubricant L is provided is prepared.

Then when the die 51, the upper punch 53, and the lower punch 54 come to a place where the spraying chamber 58 is provided by rotating the rotary table 52, pulsating vibration air is generated in the spraying chamber 58 by driving the pulsating vibration air generation means 67 and the lubricant L is sprayed from the spray nozzle 59 so as to attach on the surface (inner wall) 51*s* of the die 51, the surface (lower surface) 53*s* of the upper punch 53, and the surface (upper surface) 54*s* of the lower punch 54, as shown in FIG. 9(*a*).

As shown in FIG. 9(*b*), molding material is charged in the die 51.

Thereafter, molding material m is compressed to produce a tablet by means of the upper punch 53 and the lower punch 54 of which surfaces (lower surface 53*s* and upper surface 54*s*) are lubricated.

According to the production method disclosed in JP-A-7-124231, lubricant L can be uniformly and stably applied on the dies 51 and the punches 53, 54 by pulsating vibration air in a step of applying lubricant L so that material m is prevented from sticking on the punches 53, 54 and the die 51 and material can be continuously tabletted smoothly and stably for a long time, comparing to the production methods disclosed in JP-B-41-11273 and JP-A-56-14098.

However, according to the methods in JP-B-41-11273, JP-A-56-14098, and JP-A-7-124231, as lubricant L isn't included in a tablet, there has been problems wherein property is differed such that disintegration time becomes fast and hardness becomes high, or absorption speed of active component into body is changed.

The present invention is proposed to solve the above-mentioned problems. The object of the invention is to provide a method for producing tablet wherein molding material doesn't cause sticking and so on for the punches and the dies of the tabletting machine, tabletting can be continuously executed stably for a long time, it can be executed as an industrial tabletting method, and properties of the produced tablet such as disintegration time and hardness and absorption speed of active component into body don't differ from a tablet produced by a normal internal lubricant method. And another object of the present invention is to provide a newly constructed tablet produced according to this tablet production method.

DISCLOSURE OF THE INVENTION

According to the method for producing tablet described in claim 1, a tablet including active component, diluting agent, and lubricant is produced by means of a tabletting machine provided with punches and dies, comprising steps of; preparing molding material including active component, diluting anent, and a part of lubricant; applying most of remaining amount of the lubricant on a surface of the punch and a surface of the die; and tabletting the molding material by means of the punches on which surfaces the lubricant is applied and the die on which surface the lubricant is applied.

The term "diluting agent" in this specification means medicinal additive excluding lubricant. Namely it means that the term "diluting agent" may include excipient used for shaping a tablet (formation), supplement such as solubilizing agent, solubilizer, buffering agent, hardening agent, binder and so on other than lubricant, adjuvant such as antioxidant, preservative, aroma, sweetening agent, colorant, and so on if required.

Several kinds of lubricant can be used for the tablet production method of the present invention. Lubricant isn't specifically limited, for example, there are stearate acid metal salt (magnesium stearate, calcium stearate and so on), stearic acid, sodium lauryl sulfate, sodium lauryl magnesium, powdered gum arabic, carnauba wax, anhydrous silicic acid, magnesium oxide, silic acid hydrate, boric acid, fatty acid sodium salt, leucine, and so on which have been commonly used. One of them may be used solely or more than two of them may be combined.

According to the tablet production method of the present invention, the used amount of lubricant per a tablet is preferably adjusted to be almost the same as the lubricant amount used in an internal lubricant method.

In this specification, the term "punches" generally means a pair of an upper punch and a lower punch and "punch surfaces" means a surface of an upper punch and a surface of a lower punch when punch means a pair of an upper punch and a lower punch.

Also the term "die surface" in this specification means an inner circumferential wall of a die above an upper surface of a lower punch when the lower punch is inserted in a predetermined position in the die.

Means for applying the remaining amount of lubricant on the punch surfaces and die surface isn't particularly limited. Means disclosed in JP-B-41-11273, JP-B-48-20103, JP-A-56-14098, JP-A-59-205970, JP-A-4-295366, and JP-A-7-124231 may be used.

The method described in claim 2 concretely suggests a preferable step for applying most of the remaining amount of lubricant on the punch surfaces and the die surface.

According to the tablet production method in claim 2, in the method in claim 1, the step of applying most of remaining amount of the lubricant on the punch surfaces and the die surface is provided with a step of housing the punches and the die in a spraying chamber, and a step of spraying the most of remaining amount of lubricant while dispersing in the air in the spraying chamber.

As for the size of the spraying chamber, it is almost the same as or a little larger than the diameter of the die and also has a height for housing at least the lower surface of the upper punch positioned above the die.

Air used for spraying lubricant in the spraying chamber may be steady pressure air or pulsating vibration air.

According to the method as set forth in claim 3, in the method in claim 2, the step of spraying most of the remaining amount of lubricant in the spraying chamber is a step of spraying most of the remaining amount of lubricant while dispersing in positive steady pressure air.

The term "steady pressure air" in this specification means air of which pressure is hardly changed.

According to the method as set forth in claim 4, in the method in claim 2, the step of spraying most of the remaining amount of lubricant in the spraying chamber is a step of spraying most of the most of the remaining amount of lubricant while dispersing in positive pulsating vibration air.

"Pulsating vibration air" in this specification means air of which pressure changes with time.

"Positive pressure" in this specification means that the pressure in the spraying chamber is higher than atmosphere outside thereof.

"Positive pulsating vibration air" used in this invention includes both positive pulsating vibration air of which peak and valley are positive and positive pulsating vibration air of which peak is positive and valley is atmospheric pressure.

According to the method as set forth in claim 5, in the method in claim 1, the step of applying most of the remaining amount of the lubricant on the punch surfaces and the die surface is comprised of the steps of; housing the punches and the die in the spraying chamber; and spraying most of the remaining amount of lubricant in the spraying chamber, and applying the lubricant on the punch surfaces and the die surface while generating pulsating vibration air in the spraying chamber.

Any pulsating vibration air having several periods and strengths may be used if it can forcibly diffuse lubricant particle sprayed in the spraying chamber by generating air vibration all around therein regardless that air pressure is positive or negative.

The term "negative pressure" in this specification means that the pressure in the spraying chamber is lower than atmospheric pressure outside thereof.

"Negative pulsating vibration air" used in this invention includes both pulsating vibration air of which peak and valley are negative and pulsating vibration air of which peak is atmospheric pressure and valley is negative.

As such pulsating vibration air varies depending on the size and shape of the punches and the dies of the tabletting machine, the size and shape of the spraying chamber, attachment method of the spraying means, property of active component, and so on, it can't be generally defined so that it is defined based on experiments.

The method described in claim 6 defines the ratio of the lubricant amount included in a tablet and the lubricant applied on the punch surfaces and the die surface. It is controlled that the part of lubricant contained in the molding material as set forth in claims 1–5 is greater than or equal to about 60 weight percent and less than or equal to about 99.99 weight percent for the entire amount of lubricant used for a tablet, and the most of the remaining amount of lubricant is greater than or equal to about 0.01 weight percent and less than or equal to about 40 weight percent for the entire amount of lubricant used for a tablet.

The term "the entire amount of lubricant used for a tablet" in this specification means the used amount (weight) of lubricant for one tablet included in molding material used when a tablet is produced according to an internal lubricant method.

When most of the remaining amount of lubricant to be sprayed in the spraying chamber exceeds 40 weight % of the entire amount of lubricant used for a tablet, phenomenon such that molding material is attached on the punches and the die to cause sticking on the produced tablet is reduced. However, it isn't desirable because property and dynamic state such as absorption, and so on of the produced tablet differ from a tablet produced according to an internal lubricant method.

When most of the remaining amount of lubricant to be sprayed in the spraying chamber is less than 0.01 weight % of the entire amount of lubricant used for a tablet, it isn't desirable because phenomenon such that molding material is adhered on the punches and the die to cause sticking on the produced tablet happens at a similar frequency of an internal lubricant method.

The method as set forth in claim 7 defines the ratio of the lubricant amount included in a tablet and the lubricant applied on the punch surfaces and the die surface. It is controlled that the part of lubricant contained in the molding material described in claims 1–5 is greater than or equal to about 80 weight percent and less than or equal to about 99.99 weight percent for the entire amount of lubricant used for a tablet, and the most of the remaining amount of lubricant is greater than or equal to about 0.01 weight percent and less than or equal to about 20 weight percent for the entire amount of lubricant used for a tablet.

When the ratio of lubricant is within the above-mentioned range, properties such as disintegration time and hardness and absorption dynamic state of the produced tablet don't change comparing to a tablet produced according to an internal lubricant method.

The method described in claim 8 or claim 9 defines preferable entire using amount of lubricant.

According to the method as set forth in claim 8, the entire amount of lubricant used for a tablet in the claims 1–7 is almost the same as the entire amount used for a tablet produced by an internal lubricant method.

According to the method as set forth in claim 9, the entire amount of lubricant used for a tablet in claims 1–7 is greater than or equal to 0.01 weight percent and less than or equal to 5 weight percent for the entire weight of a tablet.

In the method described in claim 8 or 9, the amount of lubricant included in a tablet is almost the same as the entire amount of lubricant for a tablet used in an internal lubricant method. Accordingly, when the method described in claim 7 or 8 is used, a tablet of which properties such as disintegration time and hardness and absorption dynamic state don't change comparing to a tablet produced according to an internal lubricant method can be produced.

The tablet described in claim 10 defines construction of a tablet produced according to the methods described in claims 1–9.

The tablet described in claim 10 includes lubricant therein, and at least a part of lubricant applied on punch surfaces and a die surface used for molding material is accreted to the surface of the tablet with pressure.

According to the prior internal lubricant method, as lubricant is added to the molding material to be mixed, lubricant is almost uniformly applied in and on a tablet produced according to the method.

On the other hand, according to the prior external lubricant spraying method, lubricant isn't added to molding material and is applied on punch surfaces and a die surface. A tablet produced by this method doesn't include lubricant therein and at least a part of lubricant applied on punch surfaces and a die surface at the time of tabletting is accreted with pressure only on the surface of a tablet.

On the other hand, the tablet described in claim 10 includes lubricant therein and further at least a part of lubricant applied on punch surfaces and a die surface at the time of tabletting is accreted with pressure only on the surface of the tablet. A layer including lubricant per unit volume greater than the lubricant per unit volume included in the tablet is formed at an outer area of the tablet.

As the tablet described in claim 10 includes lubricant therein, disintegration characteristic and elution characteristic are similar to that of a tablet produced by the prior internal lubricant method.

Therefore, the tablet described in claim 10 can effectively prevent tabletting problems (such as sticking) because physical properties such as disintegration time and hardness and absorption dynamic state into a body of the produced tablet don't change comparing to a tablet produced by an internal lubricant method and also the lubricant density of the surface of the produced tablet is high.

BRIEF DESCRIPTION OF DRAWINGS

FIG. 3(*a*) shows construction of a spraying chamber and FIG. 3(*b*) explains a pulsating vibration air generation means.

FIG. 4(*a*) and FIG. 4(*b*) explain an example of negative pulsating vibration air respectively.

FIG. 5(*a*) explains construction of a spraying chamber and FIG. 5(*b*) explains construction of a pulsating vibration air generation means used for the tabletting machine.

FIG. 6(*a*) and FIG. 6(*b*) explain an example of positive pulsating vibration air respectively.

DISCLOSURE OF THE INVENTION

Now the tablet production method according to the present invention will be detailed hereinafter referring to the attached drawings.

Figure 1:
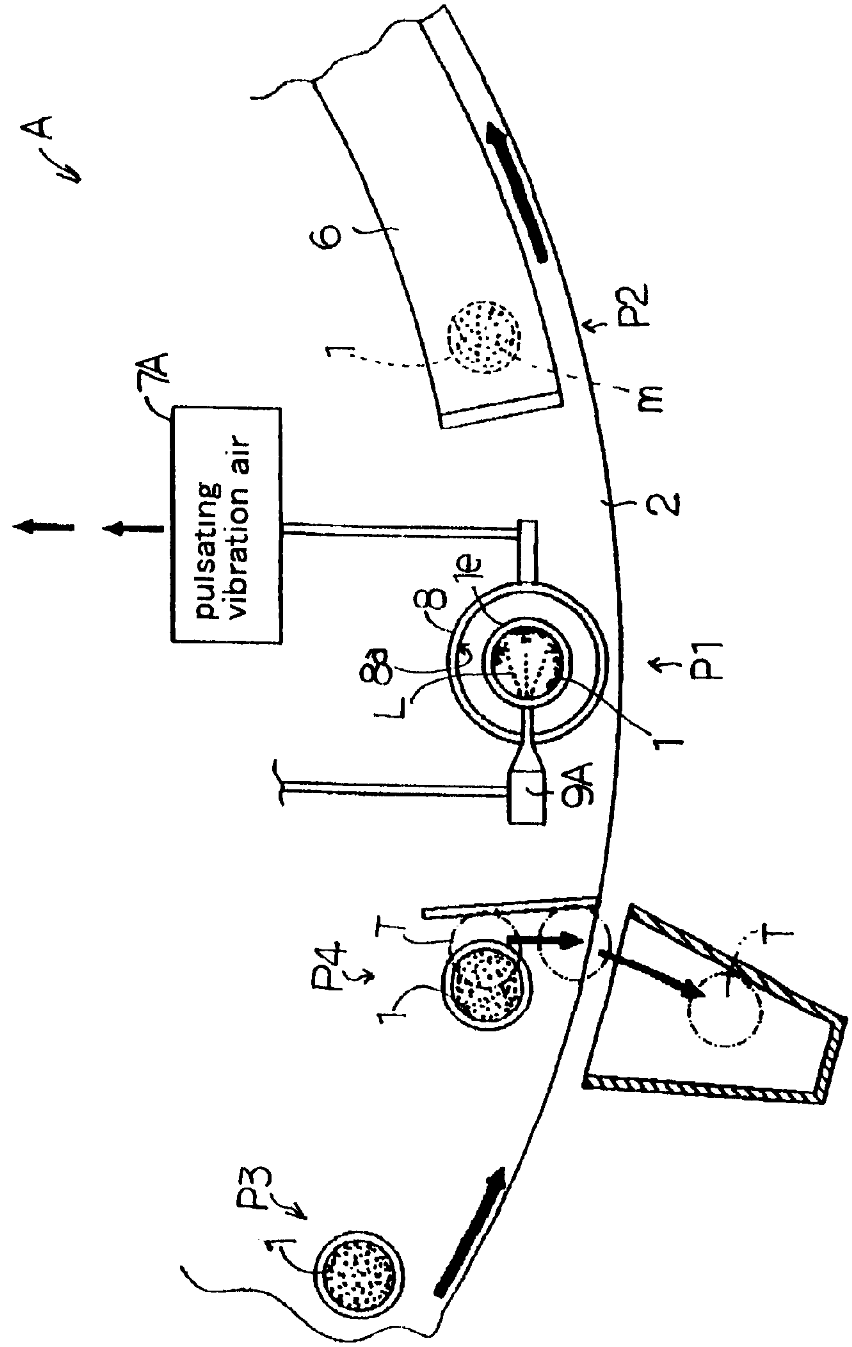
FIG. 1 shows a schematic construction of a substantial part of one embodiment of a tabletting machine used for the tablet production method according to the present invention.

FIG. 1 shows schematic construction by enlarging one part around a rotary table of a rotary type tabletting machine used for executing the present invention.

Figure 2:
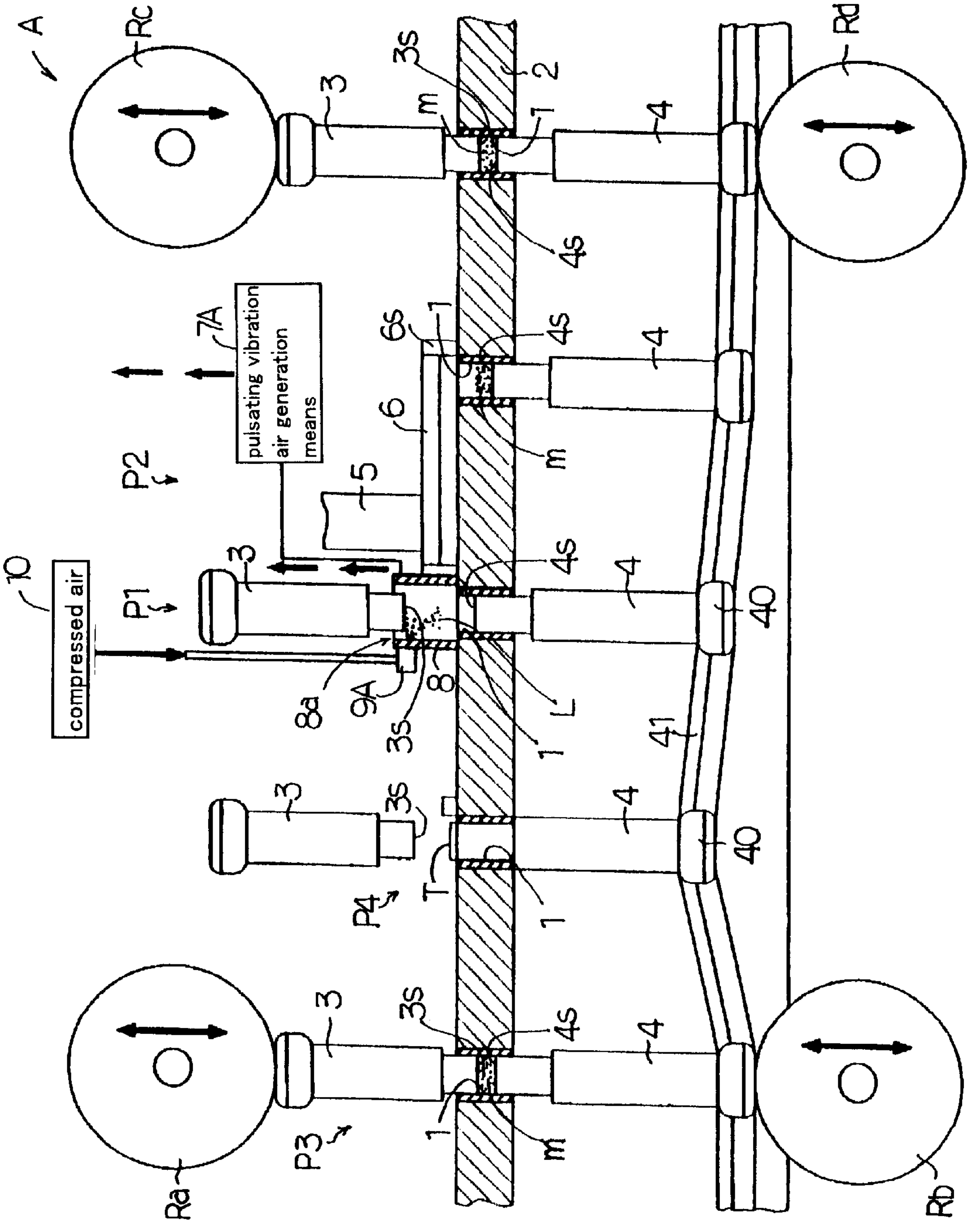
FIG. 2 is a schematic section of the substantial part of the tabletting machine shown in FIG. 1.

FIG. 2 is a schematic section when one part of FIG. 1 around the rotary table is enlarged.

As shown in FIG. 1 and FIG. 2, the tabletting machine (rotary type tabletting machine) A is comprised of a rotatably provided rotary table 2 having plural dies 1, . . . in circumferential direction, plural upper punches 3, . . . and plural lower punches 4, . . . provided so as to correspond to each die 1, . . . . A spraying chamber 8 is provided at P1 which is before a point P2 where molding material is charged in the die 1. A pulsating vibration air generation means 7A is connected to the spraying chamber 8 and a spray nozzle 9A for spraying lubricant L is provided in the spraying chamber 8.

The upper punches 3 and the lower punches 4 rotate together with the rotary table 2 while moving up and down by means of a cam 40 and a cam groove 41 and the punches 3, 4 are designed to compress molding material m charged in the dies 1.

The spraying chamber 8 is provided so as to surround from an upper circumferential end 1*e* of the die 1 to a lower surface 3*s* of the upper punch 3 positioned thereover as shown in FIG. 1 and FIG. 2. Further the spraying chamber 8 is provided with an opening 8*a* at its upper part and the upper punch 3 is designed to be inserted in a predetermined part in the spraying chamber 8 through the opening 8*a*.

At the position where the spraying chamber 8 is provided, it is designed such that the lower punch 4 comes down in the die 1 as far as possible and preferably the lower punch 4 becomes a lowest supporting point.

In this embodiment, an air source 10 such as a cylinder charged with compressed air is connected to the spray nozzle 9A and lubricant L is sprayed from the spray nozzle 9A together with compressed air by means of air generated from the air source 10.

In FIG. 2 the member indicated by a numeral 5 is a material supply chute, the member indicated by a numeral 6 shows a feed shoe, and the member indicated by a numeral 6*s* is a scraper. According to this tabletting machine (rotary type tabletting machine) A, molding material m is charged in the die 1 by means of the material supply chute 5 and the feed shoe 6 when the die 1 is positioned at the point P2 for charging molding material m accompanied with rotation of the rotary table 2 and extra molding material is scraped off by the scraper 6*s*.

In FIG. 2 the members shown as Ra, Rb indicate a roll for controlling main pressure respectively and the members shown as Rc, Rd are rollers for controlling auxiliary pressure.

According to the tabletting machine (rotary type tabletting machine) A, the height of the upper punches 3 . . . , and the lower punches 4 . . . attached with the rolls Ra–Rd are accurately controlled by controlling the height of these rollers Ra–Rd.

A nozzle which can spray a desired lubricant L in the spraying chamber 8 by supplying air pressure may be used as the spray nozzle 9A. For example, cartridge type nozzle, pressure tank type nozzle, or mini hopper type nozzle may be used.

Lubricant L isn't particularly limited if it is known one. For example there are stearic acid metal salt such as magnesium stearate and calcium stearate, sodium lauryl sulfate, talc, and soon. Kinds of lubricant L are properly selected according to molding material m.

Next tablet production method wherein molding material is hardly adhered on the punches and the dies of the tabletting machine, molding material can be continuously tabletted for a long time, and disintegration time and hardness of produced tablet don't change will be explained.

At first, the entire used amount Wa of lubricant L included in one tablet produced according to the internal lubricant method which has already obtained a permit (for example manufacturing license by Department of Health and Human Services and Food and Drug Administration) is measured.

Then the ratio of the amount Wc of lubricant L contained in molding material m and the amount We of lubricant L sprayed on the surfaces 3*s,* 4*s* of the punches and the surface (inner wall) 1*s* of the die 1 is determined.

The amount We of lubricant L for spraying the surfaces 3*s,* 4*s* of the punches 3, 4 and the surface (inner wall) 1*s* of the die 1 is preferably adjusted such that the sum of the amount Wc of lubricant L contained in molding material m and the amount We of lubricant L sprayed on the surfaces 3*s,* 4*s,* and is equals to or a little greater than the entire amount Wa of lubricant L contained per a tablet produced by an internal lubricant method ($Wa \leqq Wc+We$), anticipating the amount of lubricant L which isn't applied on the surfaces 3*s,* 4*s* and 1*s* in the spraying chamber 8 and the amount of lubricant L remained on the surfaces 3*s,* 4*s,* is without being accreted by pressure to a produced tablet when tabletting.

Actually, the amount of lubricant L sprayed in the spraying chamber 8 is varied, lubricant L is applied on the surfaces 3*s,* 4*s* of the punches 3, 4, the surface (inner wall) 1*s* of the die 1, and molding material is tabletted by means of the lubricated punches 3, 4 and die 1. The amount of lubricant L accreted by pressure on a produced tablet from the lubricated surfaces 3*s,* 4*s,* is is measured and the amount of lubricant L which isn't applied on the surfaces 3*s,* 4*s,* 1*s* in the spraying chamber 8 is adjusted.

For varying the amount of lubricant L sprayed in the spraying chamber 8, the flow amount of compressed air generated from the air source 10 and operating condition of pulsating vibration air generation means 7A may be varied.

In this tablet production method, the entire amount Wa of lubricant L is preferably greater than or equal to 0.01 weight % and less than or equal to 5 weight % of the entire weight of one tablet.

It is because that, according to an internal lubricant method, lubricant L is generally combined in molding material so as to be greater than or equal to 0.01 weight % and less than or equal to 5 weight % of the entire weight of one tablet.

The ratio of the amount Wc of lubricant L contained in a tablet and the amount We applied on the surfaces 3*s,* 4*s* of the punches 3, 4 and the surface (inner wall) is of the die 1 is preferably adjusted such that the amount Wc of lubricant L contained in molding material m is greater than or equal to 60 weight % and less than or equal to 99.99 weight % of the entire weight of lubricant L used for one tablet and the amount We of lubricant L sprayed in the spraying chamber 8 is preferably greater than or equal to 0.01 weight % and less than or equal to 40 weight % of the entire amount Wa of lubricant L used for one tablet.

Further, the ratio of the amount Wc of lubricant L contained in a tablet and the amount We applied on the surfaces 3*s,* 4*s* of the punches 3, 4 and the surface (inner wall) is of the die 1 is more preferably adjusted such that the amount Wc of lubricant L contained in molding material m is greater than or equal to 80 weight % and less than or equal to 99.99 weight % of the entire weight of lubricant L used for one tablet and the amount We of lubricant L sprayed in the spraying chamber 8 is preferably greater than or equal to 0.01 weight % and less than or equal to 20 weight % of the entire amount Wa of lubricant L used for one tablet.

Next, only the amount Wc of lubricant L to be contained molding material m is mixed in the material m.

After the above-mentioned preparation is finished, the rotary table 2 is rotated at a prescribed speed.

Next, when the die 1 is positioned at the point P1 where the spraying chamber 8 is provided accompanied with rotation of the rotary table 2, pulsating vibration air generation means 7A is driven to generate pulsating vibration air in the spraying chamber 8, lubricant L is applied on the surface (inner wall) is of the die 1, the surface (lower surface) 3*s* of the upper punch 3, and the surface (upper surface) 4*s* of the lower punch 4 by spraying lubricant L from the spray nozzle 9A.

The molding material (lubricant L is mixed therein at a ratio of amount Wc per a tablet) is charged in the die 1 at P2 positioned accompanying the rotary table 2 and extra material is scraped off.

Thereafter, when the die 1 charged with molding material m (lubricant L is mixed therein at a ratio of amount Wc per a tablet) comes to the point P3 for producing a tablet by compressing the material m, the material m is compressed to produce a tablet by means of the upper punch 3 of which surface (lower surface) 3*s* is applied with lubricant L and the lower punch 4 of which surface (upper surface) 4*s* is applied with lubricant L. Further, when the die 1 comes to the point P4, a tablet T is discharged from the die 1. In such a manner, tablets T . . . are sequentially and continuously produced.

Figure 3:
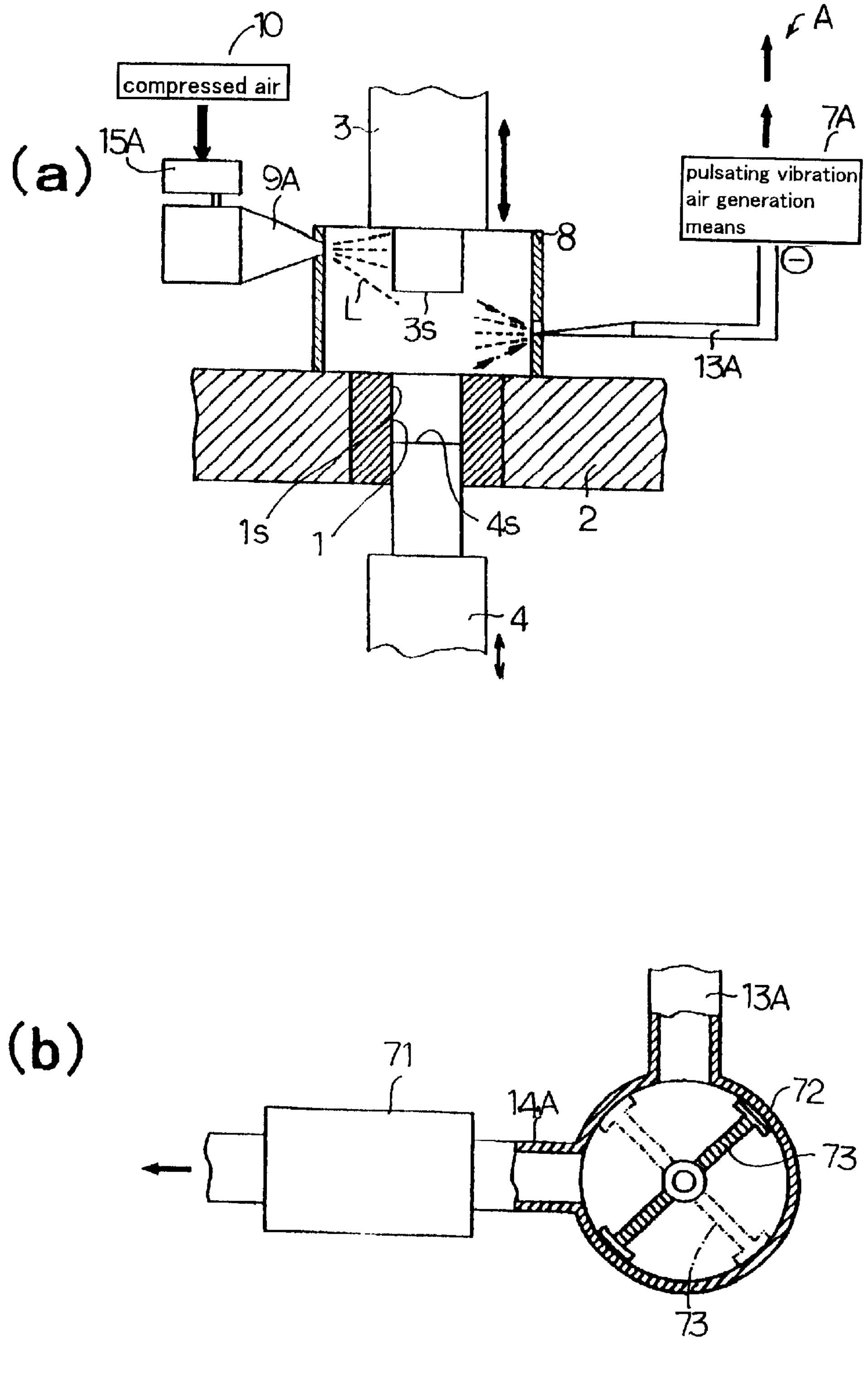
FIG. 3 is a section schematically showing an enlarged substantial part of the tabletting machine shown in FIG. 1.

FIG. 3 is an enlarged schematic section of the substantial part of the tabletting machine A. FIG. 3(*a*) shows construction of the spraying chamber 8 and FIG. 3(*b*) explains pulsating vibration air generation means 7A.

In this embodiment, the pulsating vibration air generation means 7A is connected to the spraying chamber 8 via a conduit 13A as shown in FIG. 3(*a*).

In FIG. 3(*b*), the numeral 71 indicates a blower, 72 indicates a cylindrical tube, and 73 indicates a valve element provided rotatably in the tube 72 around a rotary axis 74 so as to divide the inside of the tube 72 into two parts. The conduit 13A and a conduit 14A coupled to the blower 71 are connected at a prescribed part of the side of the tube 72.

The valve element 73 is designed to be rotated at a desired rotational velocity by a valve rotation control means (not shown).

If the blower 71 is rotated at a prescribed rotation number, current directing from the tube 72 to the blower 71 is generated in the conduit 14A.

Further, the valve element 73 is rotated at a prescribed rotational velocity while the blower 71 is rotated at a prescribed rotation number. When the valve element 73 is positioned as shown in solid line in FIG. 3(*b*), the spraying chamber 8 and the blower 71 are connected, and when the valve element is positioned as shown in dotted line, they are shut off by the valve element 73. For example, pulsating vibration air of which peak is atmospheric pressure and valley is negative pressure as shown in FIG. 4(*a*) or pulsating vibration air of which peak and valley are negative pressure as shown in FIG. 4(*b*) is generated in the spraying chamber.

Here "negative pressure" means that the pressure in the spraying chamber 8 is lower than the pressure outside of the chamber 8 (atmospheric pressure).

Figure 4:
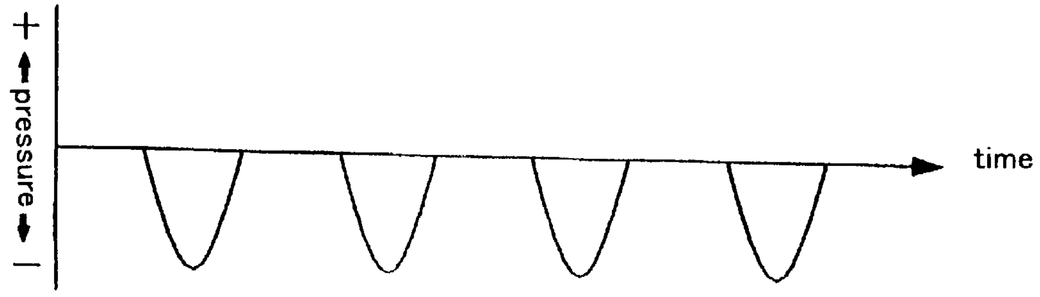
FIG. 4 shows one embodiment of a pulsating vibration air generation means.
Figure 4:
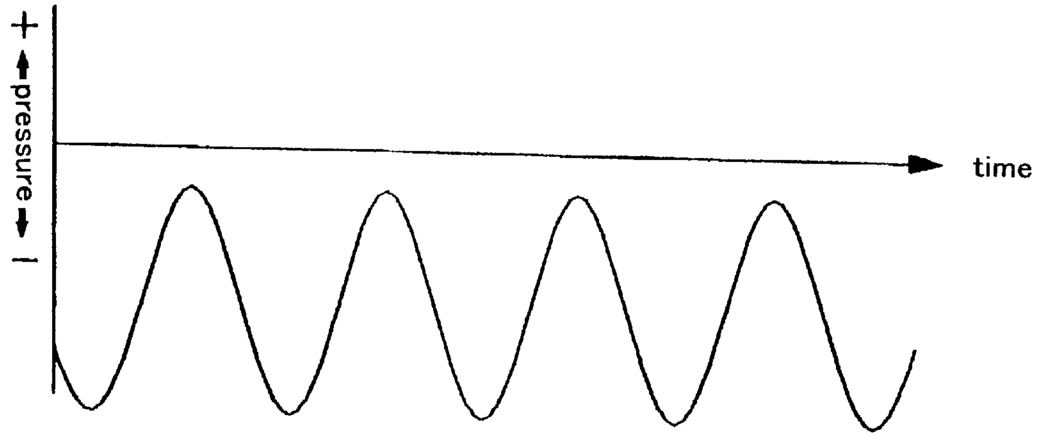

When lubricant L is sprayed from the spray nozzle 9A while pulsating vibration air shown in FIG. 4(*a*) or FIG. 4(*b*) is generated, sprayed lubricant L is diffused by means of negative pulsating vibration air.

Extra lubricant L in the spraying chamber 8 is designed to be discharged from the chamber 8 by means of negative pulsating vibration air.

As a result, lubricant L can be uniformly applied on the surface (inner wall) 1*s* of the die 1, the surface (lower surface) 3*s* of the upper punch 3 and the surface (upper surface) 4*s* of the lower punch 4 both of which are provided for the die 1 contained in the spraying chamber 8.

Further, as lubricant L can be uniformly applied on the surface (inner wall) 1*s* of the die 1, the surface (lower surface) 3*s* of the upper punch 3, and the surface (upper surface) 4*s* of the lower punch 4, even if the amount of lubricant L sprayed in the spraying chamber 8 is only minute, molding material m can be prevented from causing sticking on the dies 1 and the upper and lower punches 3, 4 of the tabletting machine A regardless of kinds of active component, diluting agent, and lubricant L. Consequently, the spraying amount of lubricant L used for one tabletting can be remarkably reduced.

According to an experiment, when the most of the remaining amount We for spraying in the spraying chamber 8 was adjusted such that the amount of lubricant L attached on one produced tablet exceeded 20 weight % of the entire amount (weight) of lubricant used for one tablet, frequency wherein molding material (lubricant L is mixed therein at a ratio of amount Wc per a tablet) was adhered on the punches 3, 4 and the die 1 while tabletting and sticking of produced tablets was caused was reduced. However, it was found to be undesirable as physical property and dynamic state such as absorption of produced tablets differed from the tablet produced by an internal lubricant method.

Further according to the experiment, when the remaining amount We for spraying in the spraying chamber 8 was adjusted such that the amount of lubricant L attached on one produced tablet was less than 0.01 weight % of the entire amount (weight) of lubricant used for one tablet, it was found that frequency wherein molding material (lubricant L is mixed therein at a ratio of amount Wc per a tablet) was adhered on the punches 3, 4 and the die 1 while tabletting and sticking of produced tablets was caused was the same as that of an internal lubricant method.

According to the tablet manufactured by the above-mentioned production method, at least a part of lubricant L applied on the surfaces 3*s*, 4*s* of the punches 3, 4 and the surface (inner wall) 1*s* of the die 1 while tabletting is accreted by pressure on the tablet surface.

That is to say, the tablet produced according to the above-mentioned method includes lubricant L inside thereof and at least a part of the accreted amount of lubricant L applied on the surfaces 3*s*, 4*s*, is is added. The tablet is constructed with a layer including lubricant of which amount per unit volume is greater than the lubricant included in the tablet.

Accordingly this tablet has a construction different from the tablet in which lubricant L is added in molding material m, mixed evenly, and compressed so that lubricant is uniformly contained in and on the tablet according to the prior internal lubricant method.

Further, it has a different construction from the tablet in which lubricant isn't included in molding material m and is applied on the surfaces 53*s*, 54*s* of the punches 53, 54 and the surface 51*s* of the die 51 in order that the tablet doesn't include lubricant therein and only a part of the lubricant applied on the punches and dies is accreted thereon by pressure according to the prior external lubricant spraying method.

As the tablet includes lubricant L, disintegration characteristic and elution characteristic thereof are approximate to that of the tablet produced according to the prior internal lubricant method.

Further, as only a little amount of lubricant L is attached on the surface of the tablet, disintegration characteristic and elution characteristic thereof are approximate to that of the tablet produced according to the prior internal lubricant method.

Therefore, when this tablet is compared to the tablet produced according to the prior internal lubricant method, property such as disintegration time and hardness of the tablet and absorption dynamic state into body don't change.

The member indicated by reference number 15A in FIG. 3(*a*) is a storage for powdered lubricant L.

In this embodiment negative pulsating vibration air shown in FIG. 4(*a*) or FIG. 4(*b*) is generated in the spraying chamber 8, however this invention isn't limited to such an air.

Figure 5:
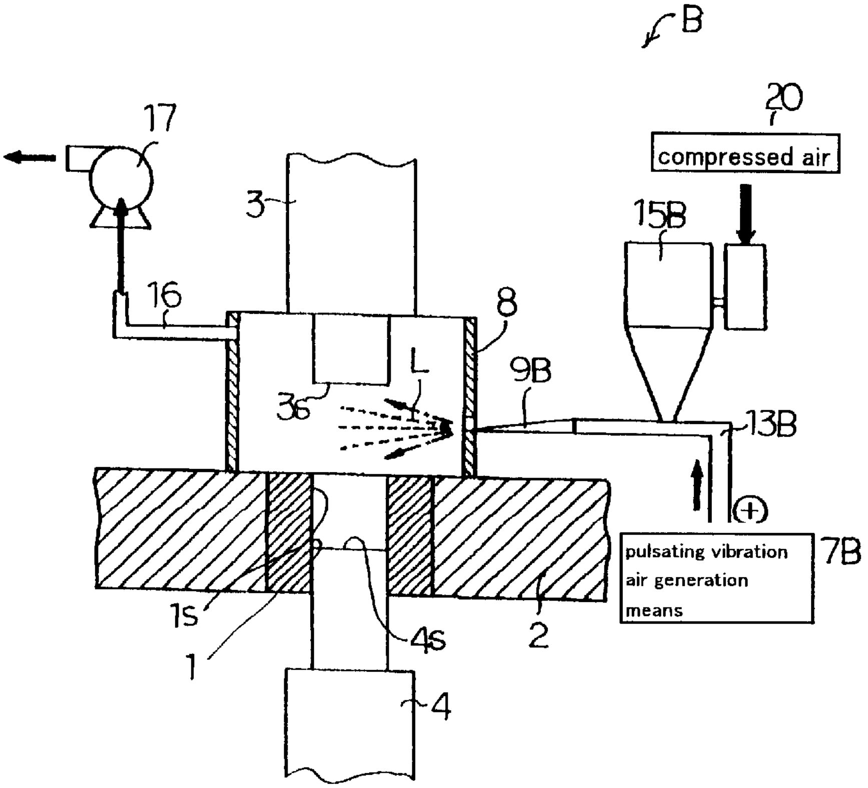
FIG. 5 is a sectional view of an enlarged substantial part of other tabletting machine preferable for the tablet production method of the present invention.
Figure 5:
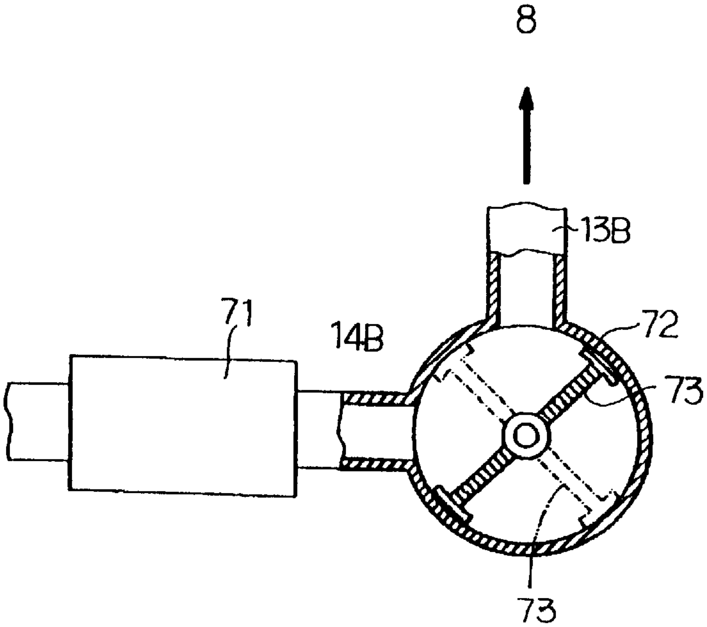

FIG. 5 is a sectional view of an enlarged substantial part of other tabletting machine preferable to the tablet production method of the present invention. FIG. 5(*a*) explains construction of the spraying chamber 8 and FIG. 5(*b*) explains construction of the pulsating vibration air generation means 7B used for the tabletting machine.

The tabletting machine (rotary type tabletting machine) B has the same construction as the tabletting machine (rotary type tabletting machine) A in FIG. 1, so the same members have the same numerals and their explanations are omitted.

According to the tabletting machine (rotary type tabletting machine) B, the pulsating vibration air generation means 7B is connected to the spraying chamber 8 via a conduit 13B.

In FIG. 5(*b*), the numeral 71 indicates a blower, 72 indicates a cylindrical tube, and 73 indicates a valve element provided rotatably in the tube 72 around a rotary axis 74 so as to divide the inside of the tube 72 into two parts. The conduit 13B and a conduit 14B coupled to the blower 71 are connected at a prescribed part of the side of the tube 72. The valve element 73 is designed to be rotated at a desired rotational velocity by a valve rotation control means (not shown).

If the blower 71 is rotated at a prescribed rotation number, current directing from the tube 72 to the blower 71 is generated in the conduit 14B.

Figure 6:
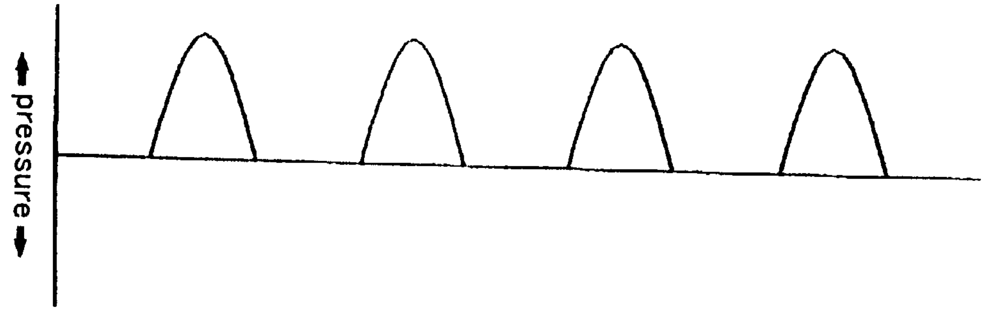
FIG. 6 shows an example of pulsating vibration air.
Figure 6:
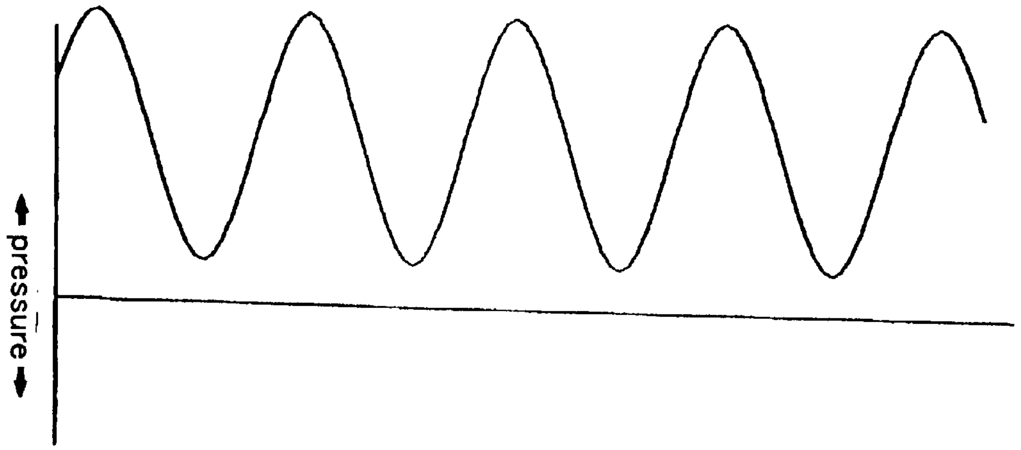
Figure 7:
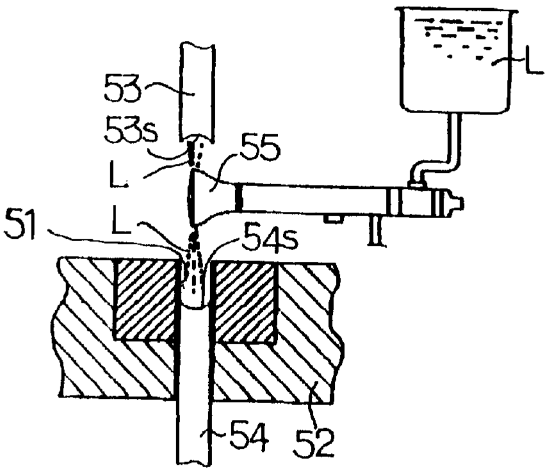
FIG. 7 schematically shows operations of the prior tablet production method disclosed in JP-B-41-11273.
Figure 7:
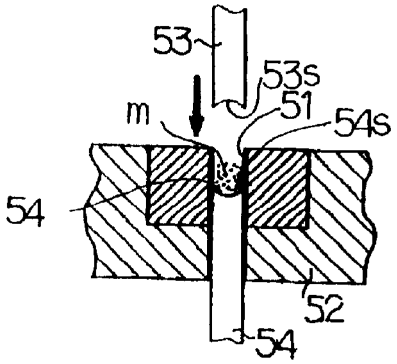
Figure 7:
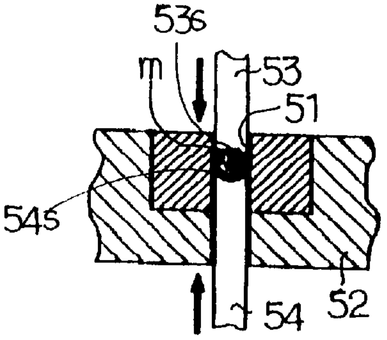
Figure 8:
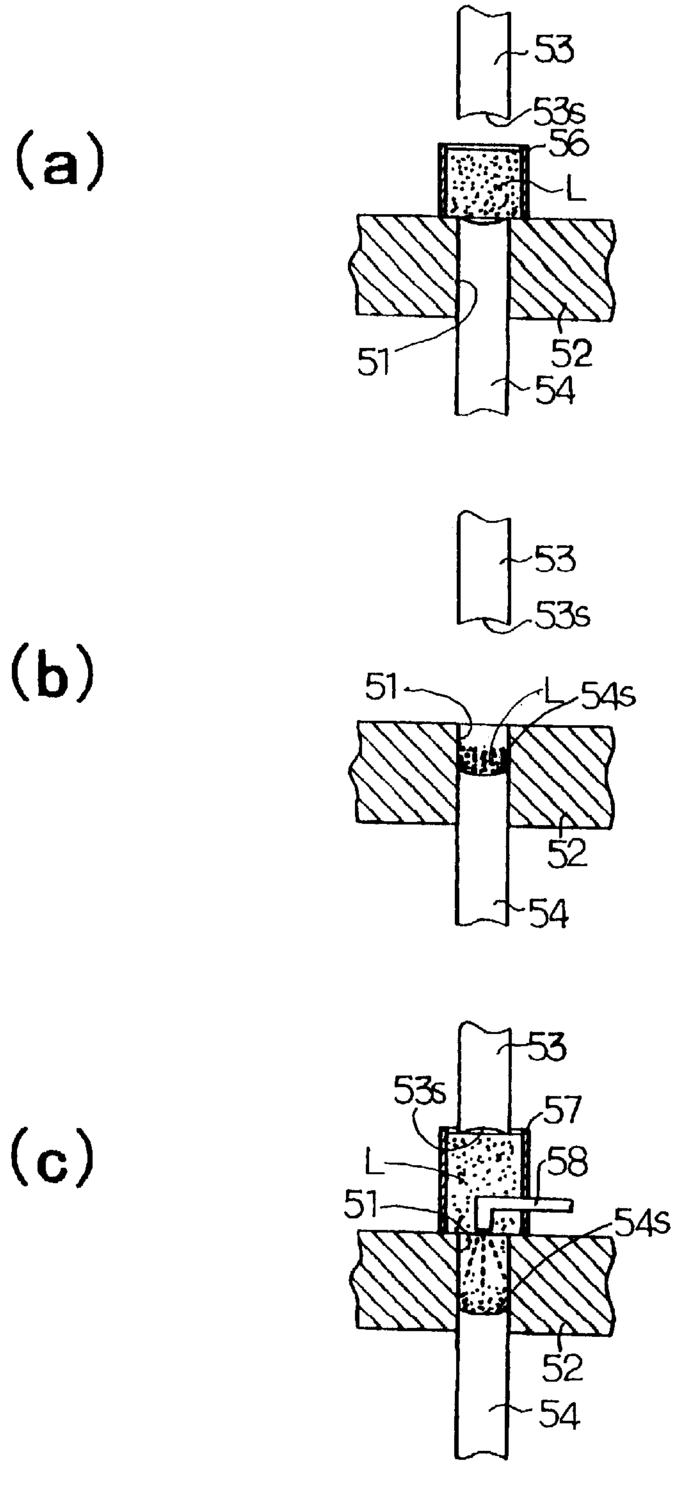
FIG. 8 schematically shows operations of the prior tablet production method disclosed in JP-A-56-14098.
Figure 9:
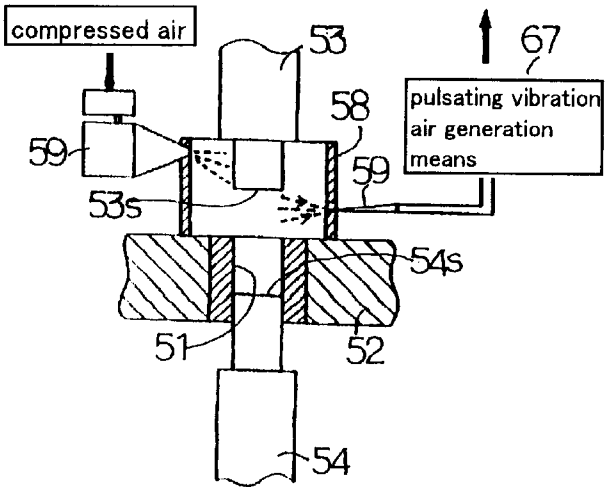
FIG. 9 schematically shows operations of the prior tablet production method disclosed in JP-A-7-124231.
Figure 9:
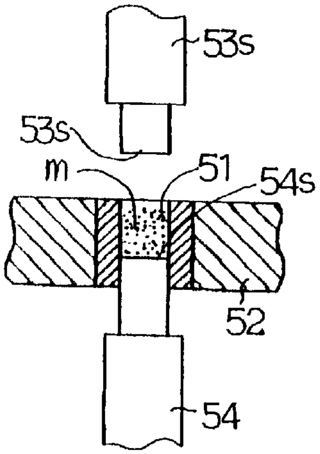
Figure 9:
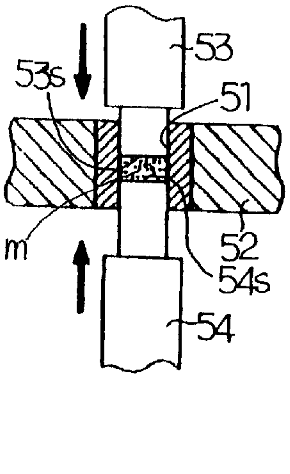

Further, the valve element 73 is rotated at a prescribed rotational velocity while the blower 71 is rotated at a prescribed rotation number. When the valve element 73 is positioned as shown in solid line in FIG. 5(*b*), the spraying chamber 8 and the blower 71 are connected, and when the valve element 78 is positioned as shown in dotted line, they are shut off by the valve element 73. For example, pulsating vibration air of which peak is positive pressure and valley is atmospheric pressure as shown in FIG. 6(*a*) or pulsating vibration air of which peak and valley are positive pressure as shown in FIG. 6(*b*) is generated in the spraying chamber 8.

Here "positive pressure" means that the pressure in the spraying chamber 8 is higher than the pressure outside of the chamber 8 (atmospheric pressure).

A spray nozzle 9B is connected at the tip end of the conduit 13B.

A hopper 15B is connected in midway of the conduit 13B (between the spray nozzle 9B and the pulsating vibration air generation means 7B).

Lubricant powder L is stored in the hopper 15B.

When positive pulsating vibration air shown in FIG. 6(*a*) or FIG. 6(*b*) is generated in the conduit 13B, lubricant powder L is discharged from the hopper 15 to the conduit 13B, mixed with positive pulsating vibration air in the conduit 13B, diffused therein, transported to the spray nozzle 9B pneumatically, then lubricant L is sprayed from the nozzle 9B with positive pulsating vibration air in the spraying chamber 8.

The lubricant sprayed in the spraying chamber 8 is diffused by positive pulsating vibration air and is uniformly applied on the surface (inner wall) 1*s* of the die 1, the surface (lower surface) 3*s* of the upper punch 3, and the surface (upper surface) 4*s* of the lower punch 4, wherein the punches 3, 4 are provided corresponding to the die 1 and all of them are contained in the spraying chamber 8.

As an air suction means 17 such as a blower is connected to the spraying chamber 8 via a conduit 16, extra lubricant L can be discharged from the spraying chamber 8 when the air suction means 17 is driven.

As a result, lubricant can be uniformly applied on the surface (inner wall) is of the die 1, the surface (lower surface) 3*s* of the upper punch 3, and the surface (upper surface) 4*s* of the lower punch 4.

Moreover, as lubricant can be uniformly applied on the surfaces 1*s*, 3*s*, 4*s*, even if the amount of sprayed lubricant is extremely a little, molding material m can be prevented from sticking on the die 1, the upper punch 3, and the lower punch 4 of the tabletting machine B regardless of kinds of active component, diluting agent, and lubricant L. As a result, spraying amount of lubricant for one tabletting can be significantly reduced.

The member shown as 20 in FIG. 5 indicates compressed air supply means for adjusting amount of lubricant powder L supplied to the conduit 13B from the hopper 15B.

When the tabletting machine B is used, appropriate amount of lubricant L can be uniformly sprayed on the surface (inner wall) 1*s* of the die 1, the surface (lower surface) 3*s* of the upper punch 3, and the surface (upper surface) 4*s* of the lower punch 4 like the case when the tabletting machine A shown in FIG. 1 is used.

Pulsating vibration air to be supplied in the spraying chamber 8 in the present invention may be positive or negative as mentioned above.

Next, the present invention will be explained based on concrete experimental data.

(Experiment 1)

According to a normal fluid-bed granulation method, glybuzole and mannitol were mixed at a ratio of 7:3, polyvinyl alcohol was sprayed, granule having a prescribed particle size and prescribed particle size distribution was manufactured, and the obtained granule was sized by means of a No.28 mesh.

Then 0.97 weight % of magnesium stearate (powder, Japanese Pharmacopoeia product) was added to the granule as lubricant L, they were well mixed by a V-type mixer, and they were tabletted to produce a 200 mg tablet at a speed of rotating a rotary table at 30 times per a minute by means of the tabletting machine A with 8 mm diameter punch and die set.

When tabletting, the punches 3, 4 and the die 1 on which surfaces 3*s*, 4*s*, is (inner wall) were applied with magnesium stearate (powder, Japanese Pharmacopoeia product) were used.

For applying magnesium stearate (powder, Japanese Pharmacopoeia product) on the surfaces 3*s*, 4*s*, 1*s*, the amount of the magnesium stearate sprayed in the spraying chamber 8 was adjusted such that weight % of lubricant L included in one produced tablet was 0.03 weight % for the entire amount of the tablet.

WSG-type 15 by Glatt Co., Ltd. was used as a fluid-bed granulator and HATA HT-X20 by Hata Seisakusho Co., Ltd. was used as a main body of a tabletting machine.

Pulsating vibration air which was always negative and frequency was 10 Hz as shown in FIG. 4(*b*) was used in the experiment 1. However such conditions aren't limited.

(Comparison 1)

Magnesium stearate was added to the granule produced like the experiment 1 as lubricant L in such a manner the amount of magnesium stearate became 1.0 weight % for the entire weight of one tablet. They were well mixed by a V-type mixer, and they were tabletted to produce a 200 mg tablet at a speed of rotating a rotary table at 30 times per a minute by means of the tabletting machine A with 8 mm diameter punch and die set.

HATA HT-X20 by Hata Seisakusho Co., Ltd. was used as a tabletting machine.

For each experiment 1 and the comparison 1, tabletting machine was continuously operated for 5 hours and produced tablet was sampled with time. Time caused sticking was measured by smoothness of the produced tablet surface.

The result is shown in a table 1

TABLE 1

| | Tabletting Pressure ($ton/cm^2$) | Hardness (kg) | time causes sticking (time) |
|---|---|---|---|
| Experiment 1 | 1 | 6 | more than 5 |
| Comparison 1 | 1 | 6 | 1 |

From the table 1, it was found that sticking wasn't occurred after 5 hours in the experiment 1, however sticking was occurred after 1 hour and tablets of which appearance was damaged were produced in the comparison 1.

It was also found from the table 1 that the tablet produced according to the present invention had the same hardness as the tablet produced by the prior internal lubricant method when material was compressed at the same tabletting pressure.

Further, disintegration test (Japanese Pharmacopoeia, general test method) and dissolution test (Japanese Pharmacopoeia, general test method) were executed for the tablets produced by the experiment 1 and the comparison 1. Both of the tablet had a similar disintegration velocity and showed similar elution curve. Accordingly, it was found that if the tablet produced according to the present invention was taken, the tablet showed similar blood level and similar bioavailability as that of the tablet produced according to the prior internal lubricant method.

(Experiment 2)

8000 g of ascorbic acid, 3200 g of lactose (DMV Co., Ltd.), 1440 g of corn starch were mixed by a fluid-bed granulator (Glatt Co., Ltd. WSG-type 15), granulated while spraying 1600 g of 10 W/W% partly saponification polyvinyl alcohol (Nippon Synthetic Chemical Industry Co., Ltd. Gohsenol EG-05), and dried.

Then the obtained granule was sized by the No.28 mesh. 0.4 weight % of magnesium stearate (Sakai Chemical Industry Co., Ltd.) was added to thus obtained granule and they were mixed for 3 minutes by a V-type mixer.

Thus obtained mixture was continuously tabletted by the tabletting machine A (HATA HT-X20 by Hata Seisakusho Co., Ltd.) shown in FIG. 1 with a 8 mm diameter punch and die set at a speed of rotating a rotary table at 30 times per a minute so as to produce a 200 mg tablet.

For tabletting, the punches 3, 4 of which surfaces 3*s*, 4*s* were applied with magnesium stearate and the die 1 of which surface (inner wall) 1*s* was applied with magnesium stearate were used.

More concretely explained, the amount of magnesium stearate sprayed in the spraying chamber 8 to be applied on the surfaces 3*s*, 4*s*, 1*s* was adjusted such that the weight % of lubricant L contained per one produced tablet became 0.1 weight % for the entire weight of one tablet. The mixture was tabletted by means of the punches 3, 4 and the die 1 of which surfaces 3*s*, 4*s*, 1*s* were applied with magnesium stearate (Sakai Chemical Industry Co., Ltd.).

In order to determine the amount of magnesium stearate sprayed in the spraying chamber 8, granule without including magnesium stearate was tabletted by varying the amount of magnesium stearate for applying on the surfaces 3*s*, 4*s* 1*s* by changing conditions of magnesium stearate sprayed in the spraying chamber 8. Thus obtained tablet was ground and magnesium stearate attached on the tablet was measured, then the condition wherein the weight % of lubricant L was 0.1 weight % for the entire weight of one tablet was selected.

In the experiment 2, pulsating vibration air which was always negative and frequency was 10 Hz as shown in FIG. 4(*b*) was used in the experiment 1. However it isn't limited.

(Experiment 3)

0.3 weight % magnesium stearate was added as lubricant L to the granule obtained according to the experiment 2 and they were mixed for three minutes by a V-type mixer.

Thus obtained mixture was continuously tabletted by the tabletting machine A (HATA HT-X20 by Hata Seisakusho Co., Ltd.) shown in FIG. 1 with a 8 mm diameter punch and die set at a speed of rotating a rotary table at 30 times per a minute so as to produce a 200 mg tablet.

For tabletting, the punches 3, 4 of which surfaces 3*s*, 4*s* were applied with magnesium stearate (Sakai Chemical Industry Co., Ltd.) and the die 1 of which surface (inner wall) is was applied with magnesium stearate were used.

More concretely explained, the amount of magnesium stearate sprayed in the spraying chamber 8 to be applied on the surfaces 3*s*, 4*s*, 1*s* was adjusted such that the weight % of lubricant L contained per one produced tablet become 0.2 weight % for the entire weight of one tablet. The mixture was tabletted by means of the punches 3, 4 and the die 1 of which surfaces 3*s*, 4*s*, 1*s* were applied with magnesium stearate (Sakai Chemical Industry Co., Ltd.).

In order to determine the amount of magnesium stearate sprayed in the spraying chamber 8, granule without including magnesium stearate was tabletted by varying the amount of magnesium stearate for applying on the surfaces 3*s*, 4*s* 1*s* by changing conditions of magnesium stearate sprayed in the spraying chamber 8. Thus obtained tablet was ground and magnesium stearate attached on the tablet was measured, then the condition wherein the weight % of lubricant L was 0.2 weight % for the entire weight of one tablet was selected.

Also in the experiment 3, pulsating vibration air which was always negative and frequency was 10 Hz as shown in FIG. 4(*b*) was used in the experiment 1. However it isn't limited.

(Comparison 2)

0.2 weight % magnesium stearate was added as lubricant L to the granule obtained according to the experiment 2 and they were mixed for three minutes by a V-type mixer.

Thus obtained mixture was continuously tabletted by the tabletting machine A (HATA HT-X20 by Hata Seisakusho Co., Ltd.) shown in FIG. 1 with a 8 mm diameter punch and die set at a speed of rotating a rotary table at 30 times per a minute so as to produce a 200 mg tablet.

For tabletting, the punches 3, 4 of which surfaces 3*s*, 4*s* were applied with magnesium stearate (Sakai Chemical Industry Co., Ltd.) and the die 1 of which surface (inner wall) is was applied with magnesium stearate were used.

More concretely explained, the amount of magnesium stearate sprayed in the spraying chamber 8 to be applied on the surfaces 3*s*, 4*s*, 1*s* was adjusted such that the weight % of lubricant L contained per one produced tablet became 0.3 weight % for the entire weight of one tablet. The mixture was tabletted by means of the punches 3, 4 and the die 1 of which surfaces 3*s*, 4*s*, 1*s* were applied with magnesium stearate (Sakai Chemical Industry Co., Ltd.).

In order to determine the amount of magnesium stearate sprayed in the spraying chamber 8, granule without including magnesium stearate was tabletted by varying the amount of magnesium stearate for applying on the surfaces 3*s*, 4*s* 1*s* by changing conditions of magnesium stearate sprayed in the spraying chamber 8. Thus obtained tablet was ground and magnesium stearate attached on the tablet was measured, then the condition wherein the weight % of lubricant L was 0.3 weight % for the entire weight of one tablet was selected.

In the comparison 2, pulsating vibration air which was always negative and frequency was 10 Hz as shown in FIG. 4(*b*) was used in the experiment 1. However it isn't limited.

Magnesium stearate contained in the tablet produced by the comparison 2 was 0.45 weight %–0.55 weight % for the entire weight of one tablet.

(Comparison 3)

0.499 weight % magnesium stearate was added as lubricant L to the granule obtained according to the experiment 2 and they were mixed for three minutes by a V-type mixer.

Thus obtained mixture was continuously tabletted by the tabletting machine A (HATA HT-X20 by Hata Seisakusho Co., Ltd.) shown in FIG. 1 with a 8 mm diameter punch and die set at a speed of rotating a rotary table at 30 times per a minute so as to produce a 200 mg tablet.

For tabletting, the punches 3, 4 of which surfaces 3*s*, 4*s* were applied with magnesium stearate (Sakai Chemical Industry Co., Ltd.) and the die 1 of which surface (inner wall) 1*s* was applied with magnesium stearate.

More concretely explained, the amount of magnesium stearate sprayed in the spraying chamber 8 to be applied on the surfaces 3*s*, 4*s*, 1*s* was adjusted such that the weight % of lubricant L contained per one produced tablet became 0.001 weight % for the entire weight of one tablet. The mixture was tabletted by means of the punches 3, 4 and the die 1 of which surfaces 3*s*, 4*s*, 1*s* were applied with magnesium stearate (Sakai Chemical Industry Co., Ltd.).

In order to determine the amount of magnesium stearate sprayed in the spraying chamber 8, granule without including magnesium stearate was tabletted by varying the amount of magnesium stearate for applying on the surfaces 3*s*, 4*s* 1*s* by changing conditions of magnesium stearate sprayed in the spraying chamber 8. Thus obtained tablet was ground and magnesium stearate attached on the tablet was measured, then the condition wherein the weight % of lubricant L was 0.001 weight % for the entire weight of one tablet was selected.

In the comparison 3, pulsating vibration air which was always negative and frequency was 10 Hz as shown in FIG. 4(*b*) was used in the experiment 1. However it isn't limited.

(Comparison 4)

Comparison 4 shows when a tablet is produced by the prior internal lubricant method.

0.50 weight % magnesium stearate was added as lubricant L to the granule obtained according to the experiment 2 and they were mixed for three minutes by a V-type mixer. Thus obtained mixture was continuously tabletted by a 8 mm diameter punch and die set at a speed of rotating a rotary table at 30 times per a minute so as to produce a 200 mg tablet.

(Comparison 5)

In the comparison 5, lubricant L wasn't included in molding material. In the example such molding material was continuously tabletted by the punches 3, 4 of which surfaces 3*s*, 4*s* were applied with magnesium stearate (Sakai Chemical Industry Co., Ltd.) and the die 1 of which surface (inner wall) 1*s* was applied with magnesium stearate.

That is, granule obtained according to the experiment 2, in which magnesium stearate wasn't included, was continuously tabletted by the tabletting machine A (HATA HT-X20 by Hata Seisakusho Co., Ltd.) shown in FIG. 1 with a 8 mm diameter punch and die set at a speed of rotating a rotary table at 30 times per a minute so as to produce a 200 mg tablet.

For tabletting, the punches 3, 4 of which surfaces 3*s*, 4*s* were applied with magnesium stearate (Sakai Chemical Industry Co., Ltd.) and the die 1 of which surface (inner wall) is was applied with magnesium stearate.

More concretely explained, the amount of magnesium stearate sprayed in the spraying chamber 8 to be applied on the surfaces 3*s*, 4*s*, 1*s* was adjusted such that the weight % of lubricant L contained per one produced tablet become 0.1 weight % for the entire weight of one tablet. The mixture was tabletted by means of the punches 3, 4 and the die 1 of which surfaces 3*s*, 4*s*, 1*s* were applied with magnesium stearate (Sakai Chemical Industry Co., Ltd.).

In order to determine the amount of magnesium stearate sprayed in the spraying chamber 8, granule without including magnesium stearate was tabletted by varying the amount of magnesium stearate for applying on the surfaces 3*s*, 4*s* 1*s* by changing conditions of magnesium stearate sprayed in the spraying chamber 8. Thus obtained tablet was ground and magnesium stearate attached on the tablet was measured, then the condition wherein the weight % of lubricant L was 0.1 weight % for the entire weight of one tablet was selected.

In the comparison 5, pulsating vibration air which was always negative and frequency was 10 Hz as shown in FIG. 4(*b*) was used in the experiment 1. However it isn't limited.

Magnesium stearate contained in the tablet produced by the comparison 5 was 0.15 weight %–0.25 weight % for the entire weight of one tablet.

(Evaluation Test)

Following evaluation tests were executed for the experiments 2, 3 and comparisons 2–5.

1. Observation of Sticking 20 tablets were sampled from the tablets discharged from the tabletting machine at 10 minutes interval for 120 minutes from start of tabletting, visual inspection by naked eye was executed, and the time before sticking was caused from starting tabletting was measured.

2. Evaluation by Disintegration Test

Disintegration test according to a general test method “disintegration test method” described in Japanese Pharmacopoeia was executed. Where water was used as test solution.

3. Evaluation by Dissolution Test

According to a general test method: "dissolution puddle method" described in Japanese Pharmacopoeia, an axis of a stirrer of a puddle method tester was rotated at 100 rpm and 900 ml water as test solution was used. One tablet was dropped in the test solution and the time till the tablet was completely disintegrated was measured and dissolution amount of ascorbic acid into the test solution per 10 minutes after the tablet was dropped in the test solution was also measured.

The results of the evaluation tests are shown in Table 2 and Table 3.

Also from the results of the table 2 and the table 3, the experiment 2 and the experiment 3 had a similar disintegration pattern as the comparison 4.

Further from the results of the table 2 and the table 3, the experiment 2 had a disintegration pattern more approximate to that of the comparison 4 comparing to the experiment 3.

On the other hand, in the comparison 2 disintegration time was longer than that of the comparison 4 and dissolution pattern was different from the comparison 4.

In the comparison 5 without including magnesium stearate therein, disintegration time was shorter than that of the comparison 4 and dissolution pattern was different from the comparison 4.

TABLE 2

| | time for causing sticking (minute) | disintegration time (minute) | amount of lubricant attached on tablet surface (weight %/tablet)* | amount of lubricant incuded in tablet (weight %/tablet) | amount of lubricant attached on tablet surface (w %/for entire amount of tablet) | amount of lubricant incuded in tablet (w %/for entire amount of tablet)* |
|---|---|---|---|---|---|---|
| experiment 2 | over 120 | 9.2 min | 0.1 | 0.4 | 20((0.1/0.5) × 100 | 80((0.4/0.5) × 100 |
| experiment 3 | over 120 | 8.6 min | 0.2 | 0.3 | 40((0.2/0.5) × 100 | 60((0.3/0.5) × 100 |
| comparison 2 | over 120 | 16.3 min | 0.3 | 0.2 | 60((0.3/0.5) × 100 | 40((0.2/0.5) × 100 |
| comparison 3 | 30 | 9.0 min | 0.001 | 0.499 | 0.2((0.001/0.5) × 100 | 99.8((0.499/0.5) × 100 |
| comparison 4 | 20 | 9.1 min | — | 0.5 | — | 100((0.5/0.5) × 100 |
| comparison 5 | over 120 | 3.1 min | 0.1 | — | 100((0.1/0.1) × 100 | |

entire amount of tablet: about 200 mg
*weight % of lubricant included in molding material before tabletting

TABLE 3

| dissolution rate of drugs | experiment 2 | experiment 3 | comparison 2 | comparison 3 | comparison 4 | comparison 5 |
|---|---|---|---|---|---|---|
| 10 min. after start of test | 31% | 27% | 3% | 32% | 29% | 83% |
| 20 min. after start of test | 78% | 77% | 36% | 78% | 81% | 98% |
| 30 min. after start of test | 95% | 95% | 72% | 98% | 96% | 99% |

According to the result of the table 2, sticking wasn't observed for the produced tablet after 120 minutes from starting of tabletting in the experiment 2, the experiment 3, the comparison 2, and the comparison 5. Contrary, in the comparison 4 according to the prior internal lubricant method, it was found that sticking was caused for the produced tablet after 20 minutes from starting of tabletting.

In the comparison 3 wherein material was tabletted in such a manner that the amount of magnesium stearate sprayed in the spraying chamber 8 to be applied on the surfaces 3*s*, 4*s*, 1*s* was adjusted such that the weight % of lubricant L contained per one produced tablet became 0.001 weight % for the entire weight of one tablet, it was found that sticking was observed for the produced tablet after 30 minutes from starting of tabletting.

From the above-mentioned results, it became apparent that the amount of magnesium stearate applied on the surfaces 3*s*, 4*s* of the punches 3, 4 and the surface (inner wall) 1*s* of the die 1 was preferably 0.001 weight % in order to prevent sticking.

From the above-mentioned results, it became apparent the ratio of the amount Wc of lubricant L contained in a tablet and the amount We applied on the surfaces 3*s*, 4*s* of the punches 3, 4 and the surface (inner wall) Is of the die 1 was preferably adjusted such that the amount Wc of lubricant L contained in molding material m was greater than or equal to 60 weight % and less than or equal to 99.99 weight % of the entire weight of lubricant L used for one tablet and the amount We of lubricant L sprayed in the spraying chamber 8 was preferably greater than or equal to 0.01 weight % and less than or equal to 40 weight % of the entire amount Wa of lubricant L used for one tablet.

Further, more accurately, it was also found that the ratio of the amount Wc of lubricant L contained in a tablet and the amount We applied on the surfaces 3*s*, 4*s* of the punches 3, 4 and the surface (inner wall) is of the die 1 was more preferably adjusted such that the amount Wc of lubricant L contained in molding material m was greater than or equal to 60 weight % and less than or equal to 99.99 weight % of the entire weight of lubricant L used for one tablet and the amount We of lubricant L sprayed in the spraying chamber 8 is preferably greater than or equal to 0.02 weight % and less than or equal to 40 weight % of the entire amount Wa of lubricant L used for one tablet.

Furthermore, it was also found that the ratio of the amount Wc of lubricant L contained in a tablet and the amount We applied on the surfaces 3*s*, 4*s* of the punches 3, 4 and the surface (inner wall) is of the die 1 was more preferably adjusted such that the amount Wc of lubricant L contained in molding material m was greater than or equal to 80 weight % and less than or equal to 99.99 weight % of the entire weight of lubricant L used for one tablet and the amount We of lubricant L sprayed in the spraying chamber 8 was preferably greater than or equal to 0.01 weight % and less than or equal to 20 weight % of the entire amount Wa of lubricant L used for one tablet.

According to the results of the experiments, it became clear that the ratio of the amount Wc of lubricant L contained in a tablet and the amount We applied on the surfaces 3$s$, 4$s$ of the punches 3, 4 and the surface (inner wall) is of the die 1 was more preferably adjusted such that the amount Wc of lubricant L contained in molding material m was greater than or equal to 80 weight % and less than or equal to 99.98 weight % of the entire weight of lubricant L used for one tablet and the amount We of lubricant L sprayed in the spraying chamber 8 was preferably greater than or equal to 0.02 weight % and less than or equal to 20 weight % of the entire amount Wa of lubricant L used for one tablet.

Similar experiments as the experiments 1–3 were executed except that the pulsating vibration air generation means 7A was stopped. In this case, although it was observed that produced tablet was apt to cause sticking more frequently, obtained tablet had similar disintegration property and dissolution property like the experiments 1–3.

Also similar experiments as the experiments 1–3 were executed except that the tabletting machine (rotary type tabletting machine) B was used instead of the tabletting machine (rotary type tabletting machine) A and positive pulsating vibration air shown in FIG. 6(*b*) was used, and it was found that its result was almost the same as that of the experiments 1–3.

Moreover, similar experiments as the experiments 1–3 were executed except that the pulsating vibration air generation means 7B was stopped. In this case, although it was observed that produced tablet showed higher tendency to cause sticking, obtained tablet had similar disintegration property and dissolution property like the experiments 1–3.

In the above-mentioned experiments, positive pulsating vibration air at 10 Hz frequency or negative pulsating vibration air at 10 Hz frequency was used. However, pulsating vibration air isn't limited to them and frequency of pulsating vibration air may be selected depending on description and particle size of lubricant L so that lubricant L is easily mixed and diffused therein.

Driving condition of the blower 71 may be set depending on the size of the spraying chamber 8 and description and particle size of the lubricant L in such a manner that lubricant L is easily mixed and diffused in air.

INDUSTRIAL APPLICABILITY

According to the method for producing tablet described in claim 1, a part of lubricant used for producing a tablet by the prior internal lubricant method is applied on the surfaces of the punches and the dies. Therefore, comparing to the tablet production method by the prior internal lubricant method, molding material can be prevented from adhering on the punches and dies of the tabletting machine and tabletting problem such as sticking is hardly caused for produced tablets.

On this account, frequency causing defective tablets can be remarkably reduced comparing to the tablet production method by the prior internal lubricant method so that productivity can be significantly improved.

Further according to the method for producing tablet described in claim 1, lubricant is included in the tablet. When the method described in claim 1 is used, a tablet of which physical property such as disintegration time and hardness and absorption dynamic state into body don't change can be effectively produced comparing to the tablet production method by the prior internal lubricant method.

That is, by using the method described in claim 1, a supplier of pharmaceutical drugs can solve tabletting problems such as sticking caused at the time of tabletting without changing bioavailablility of drugs.

According to the method described in claim 2, as the punches and the die are housed in the spraying chamber and remaining amount of lubricant diffused in air is sprayed for applying on the surfaces of the punches and the dies, lubricant can be uniformly applied. As a result, molding material is hardly adhered on the punches and the die while tabletting. Therefore, a tablet can be effectively produced by the method described in claim 2.

According to the method described in claim 3, the punches and the dies are housed in the spraying chamber and remaining amount of lubricant diffused in positive steady pressure air is sprayed for applying on the surfaces of the punches and the die, so that lubricant of constant condition can be always applied on the surfaces. As a result, molding material is hardly adhered on the punches and the dies while tabletting. Therefore, a tablet can be effectively produced by the method described in claim 3.

According to the method described in claim 4, the punches and the die are housed in the spraying chamber and remaining amount of lubricant diffused in positive pulsating vibration air is sprayed for applying on the surfaces of the punches and the die.

When remaining amount of lubricant diffused in positive pulsating vibration air is sprayed, sprayed lubricant in the spraying chamber is forcibly diffused in positive pulsating vibration air and easily attached on the surfaces of the punches and die.

If extra lubricant is attached on the surfaces of the punches and die, such extra lubricant is blown from the surfaces when pulsating vibration air is at its peak. Therefore, lubricant can be uniformly applied on the surfaces without attaching extra lubricant. As a result, molding material is hardly adhered on the punches and the die while tabletting. Accordingly, a tablet can be effectively produced by the method described in claim 4.

According to the method described in claim 5, if spraying amount of lubricant in the spraying chamber is a very little regardless of kinds of active component, diluting agent and lubricant, molding material is prevented from adhering on the punches and the die and produced tablet can be prevented from causing sticking.

Therefore, when a part of lubricant used for producing tablet by the prior internal lubricant method is applied on the surfaces of the punches and die, molding material is prevented from adhering on the punches and the dies of the tabletting machine comparing to the prior internal lubricant method so that productivity can be remarkably improved.

According to the method described in claim 6, a tablet of which property such as disintegration time and hardness and absorption dynamic state don't change can be effectively produced comparing to the tablet produced by the prior internal lubricant method.

According to the method described in claim 7, a tablet of which property such as disintegration time and hardness and absorption dynamic state are almost the same as that of the tablet produced by the prior internal lubricant method.

According to the method described in claim 8 or 9, the amount of lubricant included in a tablet is almost the same as the entire lubricant amount used for a tablet produced by the internal lubricant method. Therefore, when the method described in claim 8 or 9 is used, a tablet of which property such as disintegration time and hardness and absorption dynamic state don't change comparing to the tablet produced by the prior internal lubricant method can be effectively produced.

As the tablet described in claim 10 includes lubricant therein, property such as disintegration time and hardness and absorption dynamic state of produced tablet don't change comparing to the tablet produced by the prior internal lubricant method.

We claim:

1. A tablet including lubricant therein, wherein at least a part of lubricant applied on a surface of a punch and a surface of a die used for molding material is accreted to the surface of the tablet with pressure.

2. A method for producing tablet including active component, diluting agent, and lubricant by means of a tabletting machine provided with punches and dies, comprising steps of;

preparing molding material including said active component, said diluting agent, and a part of said lubricant;

applying most of the remaining amount of said lubricant on surfaces of the punches and a surface of the die; and tabletting said molding material by means of said punches on which surfaces said lubricant is applied and said die on which surface said lubricant is applied.

3. The method as set forth in claim 2, wherein said step of applying most of the remaining amount of said lubricant on said surfaces of said punches and said surface of said die comprises a step of housing said punches and said die in a spraying chamber, and a step of spraying most of the remaining amount of lubricant while dispersing in the air in said spraying chamber.

4. The method as set forth in claim 3, wherein said step of spraying most of the remaining amount of said lubricant dispersed in the air in said spraying chamber is a step of spraying remaining amount of lubricant while dispersing in positive steady pressure air.

5. The method as set forth in claim 3, wherein said step of spraying most of the remaining amount of said lubricant dispersed in the air in said spraying chamber is a step of spraying remaining amount of lubricant while dispersing in positive pulsating vibration air.

6. The method as set forth in claim 2, said step of applying most of the remaining amount of said lubricant on said surfaces of said punches and said surface of said die comprises the steps of;

housing said punches and said die in said spraying chamber; and spraying most of the remaining amount of said lubricant in said spraying chamber, and applying said lubricant on said surfaces of said punches and said surface of said die while generating pulsating vibration air in said spraying chamber.

7. The method as set forth in any one of claims 2–6, wherein it is controlled so that said part of lubricant contained in said molding material is greater than or equal to about 60 weight percent and less than or equal to about 99.99 weight percent for the entire amount of lubricant used for a tablet, and said most of the remaining amount of said lubricant is greater than or equal to about 0.01 weight percent and less than or equal to about 40 weight percent for the entire amount of lubricant used for a tablet.

8. The method as set forth in claim 7, wherein the entire amount of lubricant used for a tablet is adjusted to be almost the same as the entire amount of lubricant used for a tablet produced by an internal lubricant method.

9. The method as set forth in claim 7, wherein the entire amount of lubricant used for a tablet is greater than or equal to 0.01 weight percent and less than or equal to 5 weight percent for the entire weight of a tablet.

10. The method as set forth in any one of claims 2–6, wherein it is controlled so that said part of lubricant contained in said molding material is greater than or equal to about 80 weight percent and less than or equal to about 99.99 weight percent for the entire amount of lubricant used for a tablet, and said most of the remaining amount of said lubricant is greater than or equal to about 0.01 weight percent and less than or equal to about 20 weight percent for the entire amount of lubricant used for a tablet.

11. The method as set forth in claim 10, wherein the entire amount of lubricant used for a tablet is adjusted to be almost the same as the entire amount of lubricant used for a tablet produced by an internal lubricant method.

12. The method as set forth in claim 10, wherein the entire amount of lubricant used for a tablet is greater than or equal to 0.01 weight percent and less than or equal to 5 weight percent for the entire weight of a tablet.

13. The method as set forth in any one of claims 2–6, wherein the entire amount of lubricant used for a tablet is adjusted to be almost the same as the entire amount of lubricant used for a tablet produced by an internal lubricant method.

14. The method as set forth in any one of claims 2–6, wherein the entire amount of lubricant used for a tablet is greater than or equal to 0.01 weight percent and less than or equal to 5 weight percent for the entire weight of a tablet.

* * * * *

UNITED STATES PATENT AND TRADEMARK OFFICE

CERTIFICATE OF CORRECTION

PATENT NO. : 6,432,534 B1

DATED : August 13, 2002

INVENTOR(S) : Hayakawa et al.

It is certified that error appears in the above-identified patent and that said Letters Patent is hereby corrected as shown below:

Title page,
Item [57], ABSTRACT,
Line 5, “anent,” should read -- agent, --; and
Line 10, “applied” should read -- applied. --

Column 1,
Line 47, “idea,” should read -- ideas, --.

Column 2,
Line 25, “has” should read -- have a --.

Column 3,
Line 21, “anent,” should read -- agent, --.

Column 7,
Line 63, “is” should read -- is a --.

Column 8,
Line 33, “is is” should read -- 1s is --;
Lines 51 and 62, “is” should read -- 1s --.

Column 9,
Line 14, “is” should read -- 1s --.

Column 10,
Line 54, “is is” should read -- 1s is --; and

Column 12,
Lines 24 and 65, “is” should read -- 1s --.

Column 14,
Lines 20 and 53, “4s 1s” should read -- 4s, 1s --;
Line 41, “is” should read -- 1s --.

Column 15,
Lines 21 and 58, “4s 1s” should read -- 4s, 1s --.

UNITED STATES PATENT AND TRADEMARK OFFICE

CERTIFICATE OF CORRECTION

PATENT NO. : 6,432,534 B1 
DATED : August 13, 2002
INVENTOR(S) : Hayakawa et al.

It is certified that error appears in the above-identified patent and that said Letters Patent is hereby corrected as shown below:

<u>Column 16,</u>
Line 28, “is” should read -- 1s --;
Line 40, “4s 1s” should read -- 4s, 1s --;
Line 58, “minutes interval” should read -- minute intervals --; and
Line 63, “method” should read -- method: --.

<u>Column 17,</u>
Table 2, “*weight” should read -- *: weight --.

<u>Column 18,</u>
Line 37, “Is” should read -- 1s --;
Lines 49 and 61, “is” should read -- 1s --.

<u>Column 19,</u>
Line 5, “is” should read -- 1s --.

<u>Column 20,</u>
Line 16, “be always” should read -- always be --.

Signed and Sealed this

Eleventh Day of March, 2003

JAMES E. ROGAN
*Director of the United States Patent and Trademark Office*